June 11, 1957 R. E. SHEPHERD Plant Pat. 1,608
ROSE PLANT
Filed Feb. 23, 1956
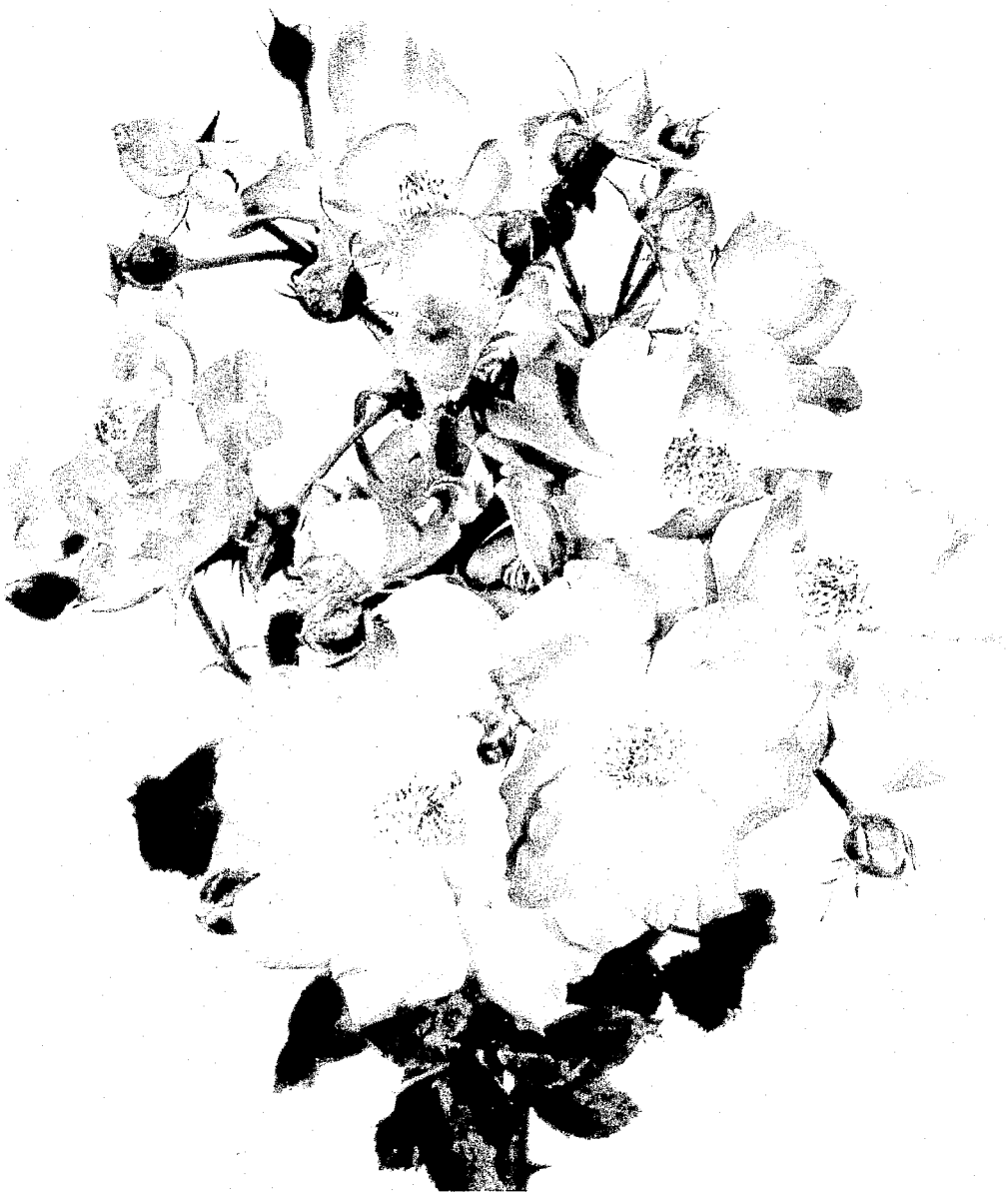
Roy E. Shepherd
INVENTOR
By Orville M. Kile
PLANT PATENT AGENT United States Patent Office Plant Pat. 1,608
Patented June 11, 1957

1,608

ROSE PLANT

Roy E. Shepherd, Medina, Ohio, assignor to Edith C. Bosley, Mentor, Ohio

Application February 23, 1956, Serial No. 567,422

1 Claim. (Cl. 47—61)

My present invention relates to an improved variety of rose plant of the floribunda type. Its parentage is Jean Lafitte (unpatented) × New Dawn (Plant Patent No. 1) × Orange Triumph (unpatented), and the crosses were made by me at my greenhouse in Medina, Ohio. Asexual reproduction by means of buds has also been accomplished by me at my greenhouse at Medina, Ohio and the predominating characteristics appear to be permanent.

The accompanying illustration shows a group of several clusters of the flowers and buds of my new variety in approximately their true colors as they appear during the winter months in the greenhouse. Flowers grown outdoors sometimes show a considerably darker color.

In the following detailed description, color plate references indicate Ridgway's Color Standards and Nomenclature, while other color names refer to the ordinary dictionary meaning.

*The plant*

Form: Compact bush.
Growth habit: Very vigorous.
Blooming habit: Exceedingly prolific producer of flowers throughout a long season.
Disease resistance: Variety is very resistant to blackspot and mildew in my greenhouse and gardens at Medina. In fact it appears to be immune from these diseases.
Foliage:
- *Quantity.*—Medium amount.
- *Size.*—Small to medium.
- *Type.*—Pinnately compound, usually with 3 to 5 leaflets.
- *Shape.*—Leaflets oval; pointed at apex. Sharply and coarsely serrated.
- *Color.*—Approximately Dark Dull Yellow Green (Pl. XXXII) in color on the upper surface, and Civette Green (Pl. XVIII) on the under surface.
- *Aspect.*—Unlike the color given in the color guide, the leaves are very glossy on their upper surface, but dull on under surface.
- *Texture.*—Thin but leathery.
- *Rachis.*—Deeply grooved and usually red-tinged on upper surface. Under surface is green and generally smooth.
- *Stipules.*—Narrow; long; clinging.

Stems:
- *Strength.*—Heavy and strong.
- *Color.*—Approximately Light Hellebore Green (Pl. XVII), with sometimes a reddish tinge.
- *Thorns.*—Stems are covered with numerous sharp, bright red thorns that are irregularly spaced and outward to downward-pointing. Many prickles and spines appear on the smaller stems and these are usually reddish-tinged. Bark on large stems between the large thorns is very smooth.

*The bloom*

Bud:
- *Size.*—Small.
- *Form.*—Ovoid.
- *Color.*—Many of the buds are red-tinged before the sepals break. As calyx breaks, the bud is approximately Spinel Red (Pl. XXVI), with a Geranium Pink (Pl. I) base. As the petals begin to open, the Geranium Pink (Pl. I) of the base blends into Rose Doree (Pl. L), with a slight accent of Scarlet Red (Pl. I).
- *Calyx.*—Large; smooth; red-tinged like stems and sepals.
- *Sepals.*—Branched. Long, "hooding" above the tight bud. Reflex partially as the bud opens.
- *Peduncle.*—Short; slender but strong; covered with fine spines which are usually red-tinged.

The flower:
- *Borne.*—In irregular, branching clusters.
- *Size.*—Averages 2½ to 3 inches across.
- *Form.*—Open; flat, sometimes cupped.
- *Color.*—The outer surface of the newly opened flower is approximately Geranium Pink at the base, blending into Rose Doree, with a slight accent of Scarlet Red at the edge. The inner surface has a large creamy-white aiglet which blends through Geranium Pink and Rose Doree, with an edge of Spectrum Red or darker. (All Plate I.) When the open flower ages, its color darkens and changes somewhat so that it then shows a blend from the creamy-white aiglet, through Deep Rose Pink, to a color at the edge which is about midway between Rose Color and Rose Red. (All Plate XII).
- *Petalage.*—Single. Has 5 to 8 petals, usually 5.

Petals:
- *Texture and aspect.*—Silky.
- *Size.*—Average is 1½ by 1½ inches.
- *Shape.*—Slightly obcordate.
- *Fragrance.*—Slight.
- *Persistence.*—Drop cleanly.
- *Lasting quality.*—Medium.

Reproductive organs:
- *Pistils.*—Tightly bunched to columnar, rising in center of green pithy ring. *Styles*—of slightly irregular lengths, rising above stamens; greenish-white. Stigmas—light yellow, approximately Pale Lemon Yellow (Plate IV).
- *Stamens.*—Many; arise from outer base of pithy ring; loosely scattered surrounding pistils, making a very large center of yellow contrasting with the color of the petals. In the later stages of flower opening, the stamens curl tightly toward pistils. Anthers are Light Cadmium (Plate IV).
- *Fruit.*—Large and colorful, producing a decorative effect even after flowers are gone.

Having thus disclosed my invention, I claim:

The new and distinct variety of floribunda rose plant, substantially as herein shown and described, characterized particularly by its vigor and hardiness; its healthy and easy growth; its exceedingly abundant production of flowers; and its showy single flowers of unique color as described.

No references cited.